United States Patent
Gijlers et al.

(10) Patent No.: US 9,207,151 B2
(45) Date of Patent: Dec. 8, 2015

(54) METHOD AND APPARATUS FOR DESORPTION OF A BLOOD SAMPLE FROM A MEDICAL TEST SHEET

(71) Applicant: SPARK HOLLAND B.V., Emmen (NL)

(72) Inventors: Hermannus Geert Gijlers, Emmen (NL); Emile Hermannus Maarten Koster, Emmen (NL); Willem Smink, Nieuwkoop (NL)

(73) Assignee: SPARK HOLLAND B.V., Emmen (NL)

( * ) Notice: Subject to any disclaimer, the term of this patent is extended or adjusted under 35 U.S.C. 154(b) by 302 days.

(21) Appl. No.: 14/050,951

(22) Filed: Oct. 10, 2013

(65) Prior Publication Data

US 2014/0037501 A1  Feb. 6, 2014

Related U.S. Application Data

(62) Division of application No. 12/899,001, filed on Oct. 6, 2010, now Pat. No. 8,586,382.

(60) Provisional application No. 61/272,997, filed on Dec. 1, 2009.

(30) Foreign Application Priority Data

Dec. 1, 2009  (EP) ..................................... 09177613

(51) Int. Cl.
*G01N 1/28* (2006.01)
*B01L 3/00* (2006.01)
(Continued)

(52) U.S. Cl.
CPC . *G01N 1/28* (2013.01); *B01L 3/505* (2013.01); *B01L 2200/0631* (2013.01);
(Continued)

(58) Field of Classification Search
CPC ............... G01N 1/28; G01N 35/1095; G01N 2030/009; G01N 2035/00128; B01L 3/505; B01L 2200/0631; Y10T 436/255; Y10T 436/25375; Y10T 436/25
See application file for complete search history.

(56) References Cited

U.S. PATENT DOCUMENTS

| 4,224,031 A | 9/1980 | Mee et al. |
| 2010/0197510 A1 | 8/2010 | Spain et al. |
| 2011/0129863 A1 | 6/2011 | Shoemaker et al. |

FOREIGN PATENT DOCUMENTS

| CH | 701 526 A2 | 1/2011 |
| EP | 2 000 800 A2 | 12/2008 |

(Continued)

OTHER PUBLICATIONS

Deglon et al.; "On-line desorption of dried blood spot: A novel approach for the direct LC/MS analysis of μ-whole blood samples;" *Journal of Pharmaceutical and Biomedical Analysis*; 2009; pp. 1034-1039; vol. 49.

(Continued)

*Primary Examiner* — Christopher A Hixson
(74) *Attorney, Agent, or Firm* — Oliff PLC

(57) ABSTRACT

A method for desorption of a blood sample from a dried blood spot on a medical test sheet, for the purpose of biomedical analysis, comprises the steps of: interposing the test sheet inbetween first and second clamping heads; clamping the first and the second clamping heads onto the interposed test sheet; and flushing a desorption area of the clamped test sheet with a sample elution fluid. The clamping heads are transmitting compressive forces to parts of the test sheet. The compressive forces create an imprinted sealing area of the test sheet, which imprinted sealing area has a closed loop shape surrounding a desorption area of the test sheet. The desorption area is contained in a space enveloped by first and second outer surfaces of the first and second clamping heads, respectively, and sealed by the imprinted sealing area.

8 Claims, 7 Drawing Sheets

(51) Int. Cl.
*G01N 35/10* (2006.01)
*G01N 30/00* (2006.01)
*G01N 35/00* (2006.01)

(52) U.S. Cl.
CPC ..... *G01N 35/1095* (2013.01); *G01N 2030/009* (2013.01); *G01N 2035/00128* (2013.01); *Y10T 436/25* (2015.01); *Y10T 436/255* (2015.01); *Y10T 436/25375* (2015.01)

(56) References Cited

FOREIGN PATENT DOCUMENTS

| | | |
|---|---|---|
| GB | 1 392 304 | 4/1975 |
| WO | WO 00/54023 A1 | 9/2000 |
| WO | WO 02/08747 A1 | 1/2002 |
| WO | WO 2011/010265 A1 | 1/2011 |
| WO | WO 2011/067221 A1 | 6/2011 |

OTHER PUBLICATIONS

Feb. 19, 2010 European Search Report issued in European Application No. 09 177 613.8.
Sep. 16, 2013 Third Party Observation for Application No. EP20090177613.
Abu-Rabie et al., "Direct Quantitative Bioanalysis of Drugs in Dried Blood Spot Samples Using a Thin-Layer Chromatography Mass Spectrometer Interface," Analytical Chemistry, vol. 81, No. 24, Dec. 15, 2009.
Van Berkel et al., "Application of a Liquid Extraction Based Sealing Surface Sampling Probe for Mass Spectrometric Analysis of Dried Blood Spots and Mouse Whole-Body Thin Tissue Sections," Analytical Chemistry, vol. 81, No. 21, Nov. 1, 2009.

METHOD AND APPARATUS FOR DESORPTION OF A BLOOD SAMPLE FROM A MEDICAL TEST SHEET

This is a Division of application Ser. No. 12/899,001 filed Oct. 6, 2010, which claims the benefit of U.S. Provisional Application No. 61/272,997 filed Dec. 1, 2009. U.S. application Ser. No. 12/899,001 also claims foreign priority to EP 09177613.8 filed Dec. 1, 2009. The disclosures of the prior applications are hereby incorporated by reference herein in their entirety.

BACKGROUND

The invention relates to a method and an apparatus for desorption of a blood sample from a medical test sheet comprising at least one dried blood spot thereon, for the purpose of biomedical analysis of the blood sample.

Such a medical test sheet may for example comprise filter paper and/or other suitable material for containing the at least one dried blood sample thereon. A widely used such medical test sheet is for example the filter paper Whatman 903®, which filter paper has a thickness of about 0.5 millimeter. Five lined-up circles are preprinted on one face of such a Whatman 903® filter paper. These circles each have a diameter of about 12 millimeter. One or more drops of blood can be placed within these circles. After drying, the filter paper thus comprises at least one dried blood spot thereon.

In order to analyse such a dried blood spot, at first, compounds need to be extracted from the filter paper. For that purpose, according to usual practice, a disc area corresponding to a preprinted circle on the filter paper containing dried blood sample, or of smaller diameter than that of the preprinted circle, is punched out of the filter paper.

Traditionally, the punched-out disc is then placed into a little tray, bottle, other container, or the like. The extraction procedure is then carried out by an organic solvent or a mixture of water thereof, containing an internal standard (IS). Traditionally, after extraction and centrifugation, the supernatant is collected and analysed by liquid chromatography mass spectrometry.

More recently, another concept has been described in the article Julien Déglon, Aurélien Thomas, Antonio Cataldo, Patrice Mangin, Christian Staub, "*On-line desorption of dried blood spot: A novel approach for the direct LC/MS analysis of μ-whole blood samples*", Journal of Pharmaceutical and Biomedical Analysis 49(2009) 1034-1039. Said article presents a new concept allowing the direct analysis of a dried blood spot coupled to a liquid chromatography mass spectrometry device (LC/MS). According to this new concept, a 10 millimeter disc containing dried blood sample is punched out of the filter paper sheet and an IS solution is added directly on the dried blood sample. Then, the blood disc is placed into a desorption cell, which is an inox cell that comprises two parts which can be brought in sealing engagement with each other via a separate sealing ring. The separate sealing ring has external-internal diameters of 14 and 12 millimeter, respectively, and thickness of 1.5 millimeter. The cell is then integrated into an LC/MS system where the analytes are desorbed out of the paper towards a column switching system ensuring the purification and separation of the compounds before their detection on a single quadrupole MS coupled to atmospheric pressure chemical ionisation (APCI) source. This new concept presented in said article is called "on-line" desorption of dried blood spots ("on-line DBS"), to indicate its distinction from the above-described traditional "off-line" extraction, in which compounds need to be extracted from the filter paper disc prior to analysis.

SUMMARY

It is an object of the invention to provide a solution according to which on-line desorption of dried blood spots is faster and easier and allows for further automation of the process.

For that purpose, the invention provides a method according to claim 1, as well as an apparatus according to claim 7. Specific embodiments of the invention are set forth in the dependent claims.

Thus, the invention allows for interposal of the test sheet inbetween the clamping heads, which will then clamp onto the interposed test sheet. Then, the desorption area of the clamped test sheet may be flushed with the sample elution fluid in such manner that the blood sample is desorbed and eluted from the desorption area. So, there is no need for first punching-out a disc area of the test sheet containing dried blood sample. This is speeding up the procedure considerably. Furthermore, there is no need for making use of a separate sealing element, since the sealing is provided by part of the test sheet, i.e. in the form of the automatically generated imprinted sealing area of the test sheet. In clamped condition this imprinted sealing area seals the desorption area, which is located interior of the closed loop formed by the imprinted sealing area, from portions of the test sheet located exterior of said closed loop.

In a preferable embodiment of a method according to the invention, the test sheet in said clamped condition is sandwiched inbetween a first cover sheet and a second cover sheet. The first and second cover sheets may be clean sheets, not containing blood sample. Such use of such first and second cover sheets contributes to keeping the first and second clamping heads clean. These first and second cover sheets may be made of various materials, they may for example be made of or at least comprise filter paper.

In another preferable embodiment, the method according to the invention further comprises the step of injecting the desorbed and eluted blood sample together with a mobile phase into analyzing means for realizing said biomedical analysis, wherein said sample elution fluid functions as said mobile phase and wherein said flushing of the desorption area and said injecting into the analyzing means are simultaneously driven by the action of a pumping means, such as a gradient pump or a high pressure dispenser. This allows for a simple configuration for performing the biomedical analysis of blood samples.

In another preferable embodiment, the method according to the invention further comprises the steps of: temporarily storing at least the desorbed and eluted blood sample in a sample loop; and injecting at least part of the blood sample stored in the sample loop, together with a mobile phase, into analyzing means for realizing said biomedical analysis, wherein said storing and said injecting is controlled by switching of valve means. This allows for performing versatile and powerful biomedical analyses of blood samples. That is, characteristics of the sample elution fluid and the mobile phase, respectively, as well as their flow properties, respectively, may be optimized independently of one another.

In a further preferable embodiment, the sample loop comprises a solid phase extraction cartridge. This allows for clean-up of the eluted blood sample by solid phase extraction. Thus, undesired compounds of the blood sample may be removed prior to analysis. Such additional cleaning-up of the blood sample removes detection interference.

In a preferable embodiment of the apparatus according to the invention, the compressive movement mechanism is arranged for moving the first and the second clamping heads towards one another in such manner that in the clamped condition the shortest possible distance between the first and the second outer surfaces is less than 0.5 millimeter, preferably less than 0.2 millimeter, more preferably less than 0.05 millimeter.

In another preferable embodiment of the apparatus according to the invention, the first outer surface and the second outer surface are substantially mirror images from one another. Since the first and second outer surfaces are facing towards one another, this allows for manufacturing the first and the second clamping heads as substantially identical to one another.

Preferably, at least one of said first and said second outer surfaces has at least partly undergone an electrolytic polishing treatment. This not only improves hygiene, but also improves the sealing performance of the imprinted sealing area of the test sheet.

In another preferable embodiment, the non-flat shape of the at least one of the first and second outer surfaces is arranged such that the shortest possible distance, measured along the imprinted sealing area of the test sheet when travelling from portions of the test sheet interior of said closed loop to portions of the test sheet exterior of said closed loop, is at least 1.0 millimeter. In this way a reliable sealing performance of the imprinted sealing area of the test sheet is obtained under relatively high fluid pressures occurring during the flushing.

In another preferable embodiment, transition portions of the at least one of the first and second outer surfaces, which transition portions in the clamped condition are adjacent to and determine the transition between the imprinted sealing area and the desorption area of the test sheet, are rounded off. This prevents that, under relatively high fluid pressures occurring during the flushing, parts of the desorption area of the test sheet would be teared off from the test sheet.

Preferably, the apparatus further comprises: analyzing means for realizing said biomedical analysis; pumping means for realizing said flushing and injection of at least part of the desorbed and eluted blood sample together with a mobile phase into the analyzing means; and a fluid conduit structure for realizing fluid communication at least between the pumping means, the first and second fluid conduits, and the analyzing means.

In another preferable embodiment, the apparatus further comprises an automatic test sheet handling system comprising at least one magazine for storing a plurality of such test sheets, and a pick and place mechanism for: at least picking up test sheets from the at least one test sheet magazine; interposing such test sheet inbetween the clamping heads; precise positioning of such interposed test sheet relative to the clamping heads; moving such test sheet away from the clamping heads; and storing or discarding such test sheet. Thus, a very high automation level of the process is achieved.

Further details, aspects and embodiments of the invention will be described, by way of example only, with reference to the schematic figures in the enclosed drawing.

DETAILED DESCRIPTION OF THE EMBODIMENTS

Figure 1:
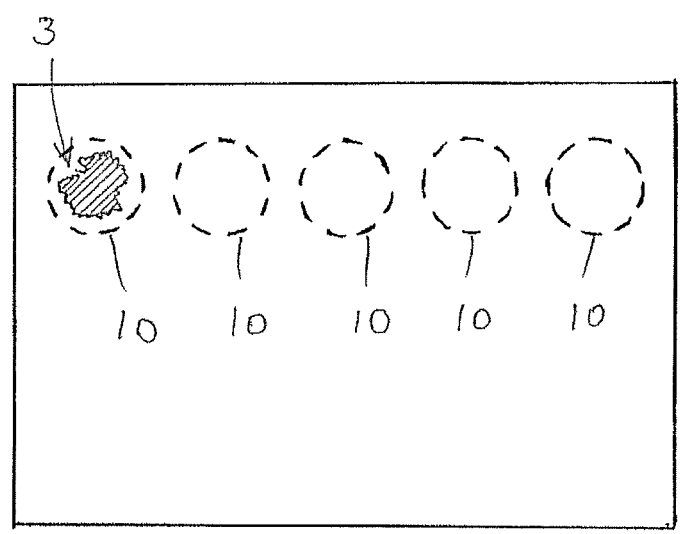
FIG. 1 shows, in upper view, an example of an embodiment of a medical test sheet, comprising a dried blood spot thereon, for use with a method according to the invention.

Note, that for the different embodiments shown in the different figures, sometimes the same reference numerals have been used to indicate parts or aspects which are similar for the different figures.

The medical test sheet 2 of FIG. 1 is made of filter paper and has a sheet thickness of about 0.5 millimeter. Although such type of test sheet is most commonly used in practice, other suitable materials for the test sheet and other sheet thicknesses (for example about 0.25, 0.75 or 1.0 millimeter or other thicknesses in this relatively small order of magnitude) are possible.

As shown in FIG. 1, one face of the test sheet 2 is provided with a number of preprinted circles 10, indicating to users the areas on which drops of blood can be placed. In FIG. 1, within the interior of the leftmost circle 10, the test sheet 2 comprises a dried blood spot 3 thereon. Test sheet 2 has a first face 11 and an opposing second face 12, see FIG. 3. The dried blood spot 3 generally is extending throughout the whole thickness of the sheet 2, and will generally also appear more or less as a crust on one or both faces 11, 12 of the sheet 2.

Figure 2:
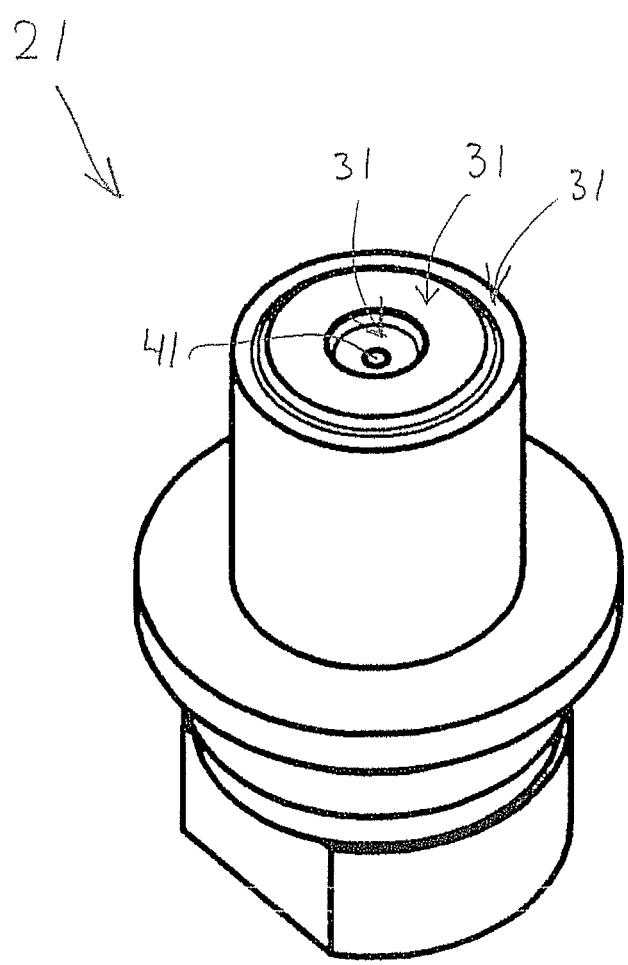
FIG. 2 shows, in a perspective view, an example of an embodiment of a first clamping head for use with a method according to the invention.

FIG. 2 shows first clamping head 21 having first outer surface 31. In the shown examples, the second clamping head 22 is substantially identical to the first clamping head 21 and has a second outer surface 32, the first and second outer surfaces facing towards one another. This amongst others implies that, in the shown example the first outer surface 31 and the second outer surface 32 are substantially mirror images from one another.

Figure 3:
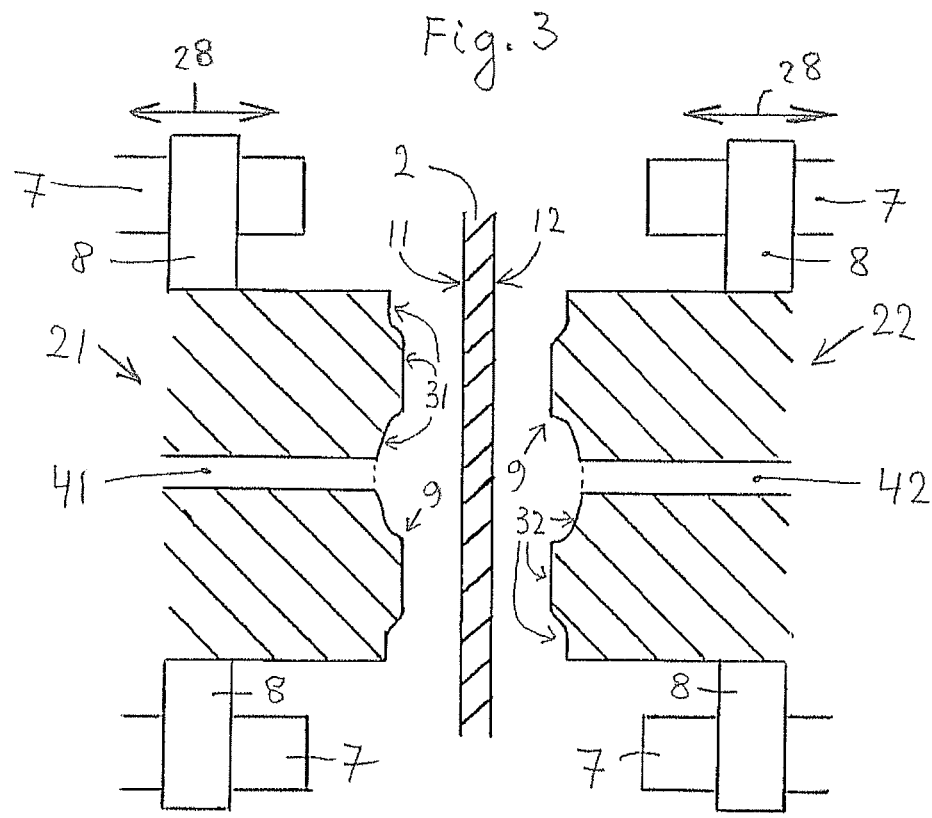
FIG. 3 shows, in a mid-longitudinal section, an example of an embodiment of first and second clamping heads, with the test sheet of FIG. 1 interposed therebetween, for use with a method according to the invention.

In FIG. 3 it is shown that the test sheet 2 has been interposed inbetween the first and second clamping heads 21, 22 in such manner that the first face 11 of the test sheet 2 is facing towards the first outer surface 31, while the second face 12 of the test sheet 2 is facing towards the second outer surface 32.

Figure 4:
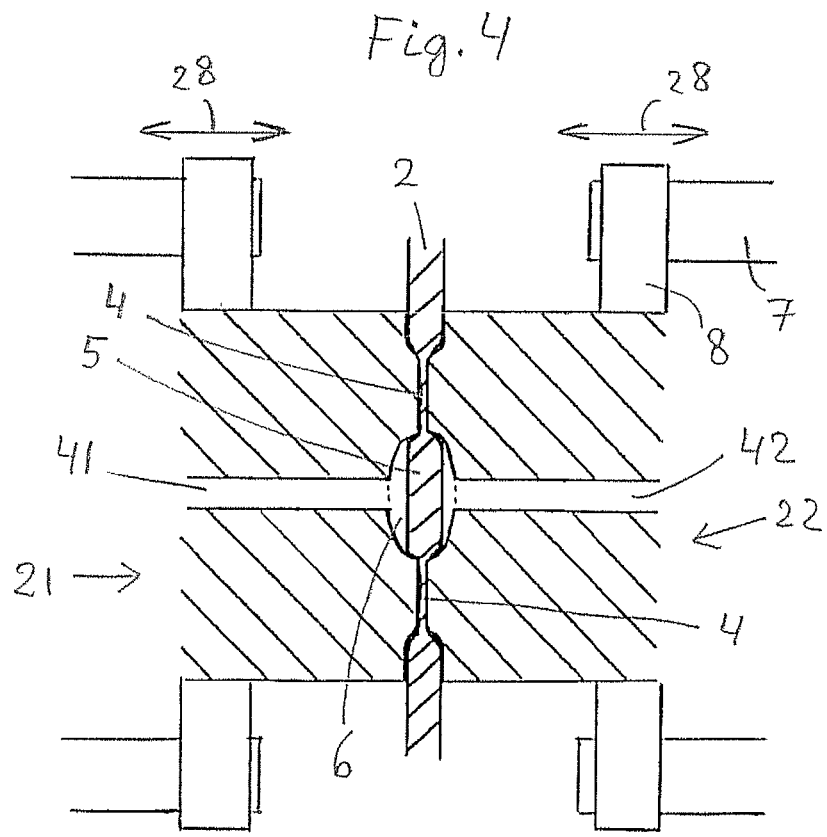
FIG. 4 shows the example of FIG. 3 once again, however, with the first and second clamping heads in clamped condition.

FIGS. 3 and 4 furthermore show part of a compressive movement mechanism arranged for selectively moving the first and the second clamping heads 21, 22 towards and away from one another, respectively, and arranged for imparting compressive forces to the first and the second clamping heads 21, 22 for clamping the test sheet 2 inbetween the first and the second clamping heads 21, 22. In the shown example, the compressive movement mechanism comprises slides 8, each being fixed relative to a concerning clamping head 21 or 22, as well as guides 7. The slides 8 are moveable to and fro along the guides 7 as indicated by double arrows 28. Instead of the shown configuration, the compressive movement mechanism may of course have such slides 8 and guides 7 only for one of the first and the second clamping heads, the other one of the first and the second clamping heads not being moveable relative to a referential outside environment.

FIG. 4 shows the clamped condition. In that condition, part of the first face 11 of the test sheet 2 is contacting the first outer surface 31 of the first clamping head 21, while part of the second face 12 of the test sheet 2 is contacting the second outer surface 32 of the second clamping head 22. From FIGS. 3 and 4 it can also be seen that the first and second outer surfaces 31, 32 each have a non-flat shape in such manner that the first and second clamping heads 21, 22 in the clamped condition are transmitting the compressive forces to parts of the test sheet 2, which compressive forces create an imprinted sealing area 4 of the test sheet, which imprinted sealing area has a closed loop shape surrounding a desorption area 5 of the test sheet.

It is remarked that, as mentioned above, the test sheet in the clamped condition may be sandwiched inbetween a first cover sheet and a second cover sheet. In FIGS. 3 and 4, such embodiment with such first and second cover sheets has not been shown for reasons of simplicity. However, for such embodiment it will be clear that in the clamped condition of FIG. 4, such first cover sheet may be in interposed position inbetween the sheet 2 and the first clamping head 21, while such second cover sheet may be in interposed position inbetween the sheet 2 and the second clamping head 22.

In FIG. 4 it is assumed that the sheet 2 has been positioned relative to the clamping heads 21, 22 in such manner that the shown desorption area 5 contains at least part of the dried blood spot 3. For simplicity, the dried blood spot 3 has not been indicated in FIGS. 3 and 4. As mentioned above, the dried blood spot 3 may partly appear more or less as a crust on one or both faces 11, 12 of the sheet 2. In FIG. 4, the desorption area 5 of the test sheet is contained in the space 6 enveloped by the first and the second outer surfaces 31, 32 and sealed by the imprinted sealing area 4.

As shown in FIGS. 2-4, the first clamping head 21 comprises a first fluid conduit 41 extending therethrough and the second clamping head 22 comprises a second fluid conduit 42 extending therethrough. Each of the first and second fluid conduits 41, 42 are ending in said enveloped space 6 containing the desorption area 5 of the test sheet 2, for flushing the desorption area 5 of the clamped test sheet 2 with a sample elution fluid in such manner that the blood sample is desorbed and eluted from the desorption area 5, said flushing taking place via the first fluid conduit 41 and the second fluid conduit 42. During such flushing, the desorption area 5 of the sheet 2 will normally swell, and consequently acquire more sheet thickness. Because of that swelling, the desorption area 5 will nicely be embedded in the enveloped space 6, portions of the first and the second outer surfaces 31, 32 supporting the swollen desorption area 5. This supported embedding of the desorption area in the enveloped space 6 aids in preventing that, under relatively high fluid pressures occurring during the flushing, parts of the desorption area of the test sheet would be teared off from the test sheet. For simplicity, said swelling of the desorption area has not been shown in FIG. 4.

Figure 5:
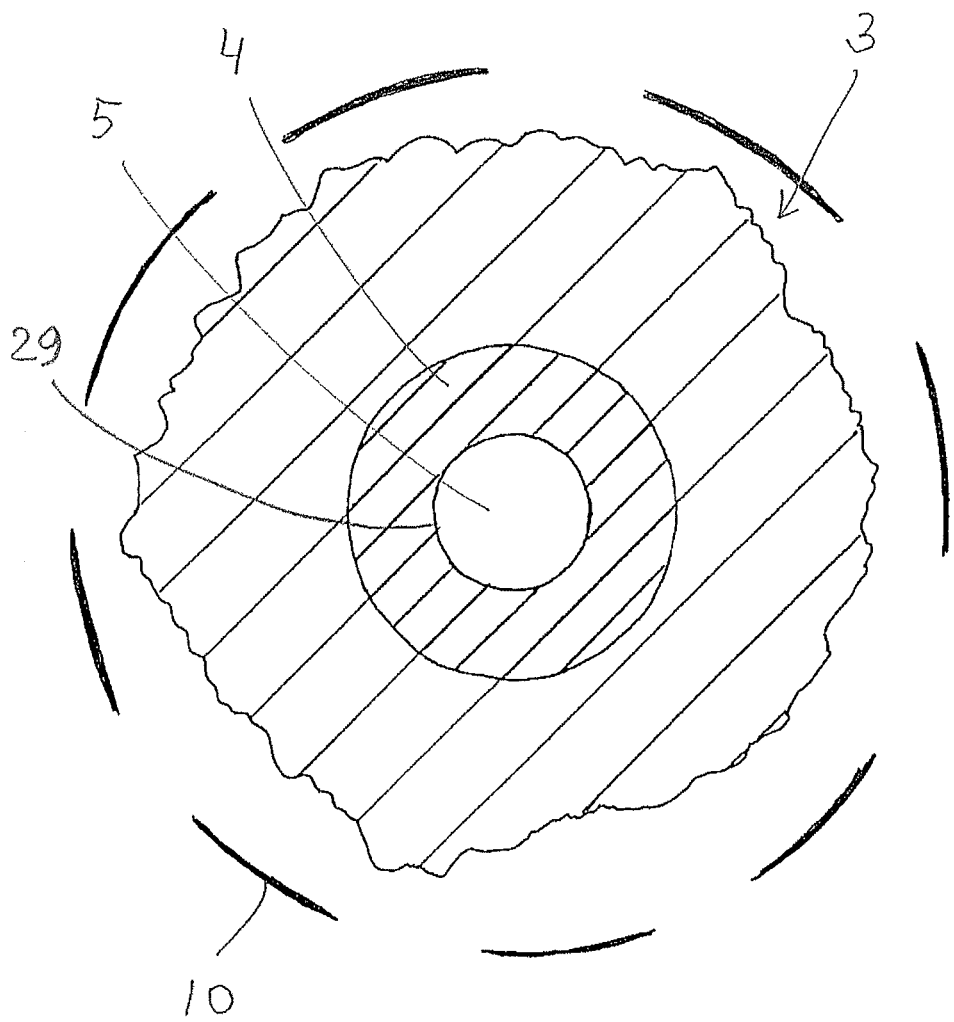
FIG. 5 shows, in upper view, a part of the example of FIG. 1 once again, however, in a condition in which blood sample of the dried blood spot on the test sheet has been desorbed and eluted from the test sheet using a method according to the invention.

FIG. 5 shows the dried blood spot 3 after blood sample has been desorbed and eluted from the desorption area 5. In FIG. 5 the desorption area 5, not containing blood sample anymore, is shown in an unhatched manner. The remaining parts of the sheet that still contain blood from the dried blood spot 3, are indicated in hatched manner. The imprinted sealing area 4 has been indicated with a more dense hatching.

In view of the above explained test sheet thicknesses having a relatively small order of magnitude, the compressive movement mechanism 7, 8 is arranged for moving the first (21) and the second (22) clamping heads towards one another in such manner that in the clamped condition the shortest possible distance between the first (31) and the second (32) outer surfaces is less than 0.5 millimeter, preferably less than 0.2 millimeter, more preferably less than 0.05 millimeter.

In the shown example, the non-flat shapes of the first 31 and second 32 outer surfaces are arranged such that the maximum diameter of the desorption area 5 is about 2.0 millimeter, while the maximum diameter of the imprinted sealing area 4 is about 4.5 millimeter. Thus the shortest possible distance, measured along the imprinted sealing area 4 of the test sheet 2 when travelling from portions of the test sheet interior of said closed loop to portions of the test sheet exterior of said closed loop, is about 1.25 millimeter. This satisfies the above mentioned criterion that said shortest possible distance preferably is at least 1.0 millimeter, thus giving a reliable sealing performance of the imprinted sealing area of the test sheet under relatively high fluid pressures occurring during the flushing.

FIG. 5 shows the transition 29 between the imprinted sealing area 4 and the desorption area 5 of the test sheet 2. Preferably, transition portions 9 (see FIG. 3) of the first 31 and second 32 outer surfaces; which transition portions 9 in the clamped condition are adjacent to and determine said transition 29, are rounded off. In the shown example, a rounding off with a radius of curvature of about 0.05 millimeter has turned out to be successful in preventing that, under relatively high fluid pressures occurring during the flushing, parts of the desorption area of the test sheet would be teared off from the test sheet.

Figure 6:
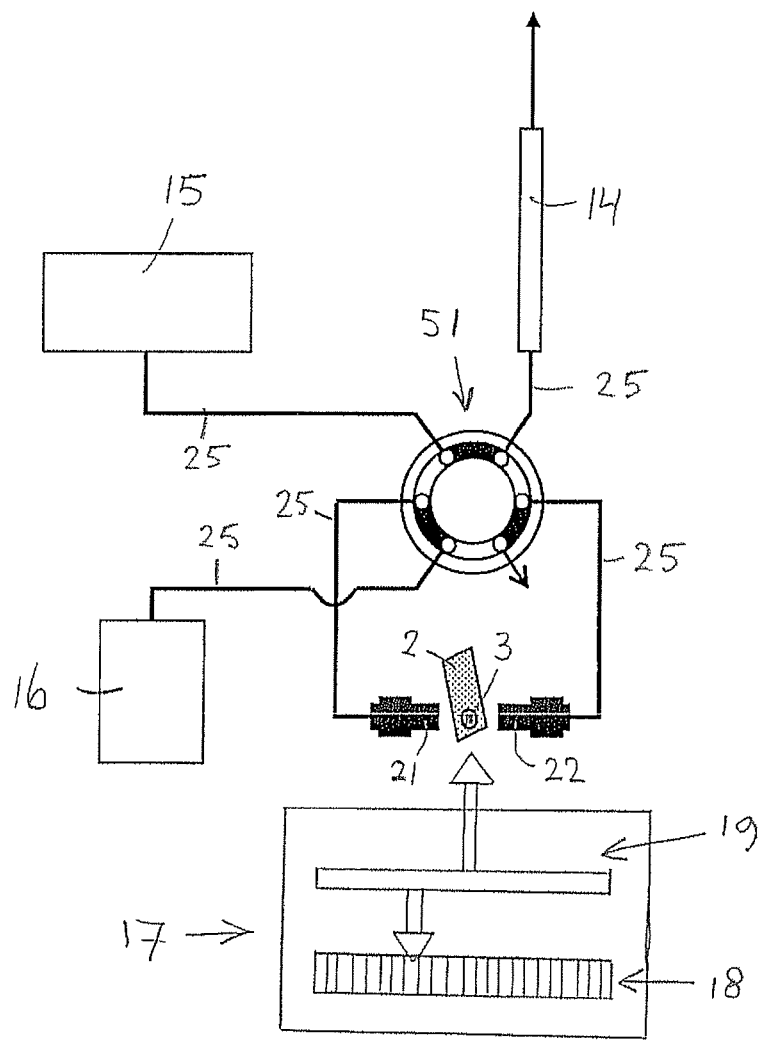
FIG. 6 shows an example of an embodiment of an apparatus for use in an example of an embodiment of a method according to the invention.

Reference is now made to FIG. 6, which shows apparatus 1 comprising the above described first and second clamping heads 21, 22. Although for simplicity not shown in FIG. 6, the apparatus 1 also comprises a compressive movement mechanism, such as the above described mechanism comprising the slides 8 and guides 7. The apparatus 1 further comprises analyzing means, in this example a liquid chromatography column 14, a gradient pump 15, a dispenser 16 and a six-port valve 51 of the stator/rotor type. FIG. 6 also shows a fluid conduit structure 25 for realizing fluid communication between the first and second fluid conduits 41, 42 of the clamping heads 21, 22, the valve 51, the column 14, the gradient pump 15 and the dispenser 16.

It is remarked that the present document makes use of the following nomenclature for two different valve positions of the valve 51.

The "black position" of the valve 51 refers to the valve position in which each of the shown three black-filled ring segments of the six-port valve serves as a fluid channel that provides fluid communication between the valve ports to which the concerning ring segment is connected. In the black position the three white-filled ring segments of the six-port valve do not provide such fluid communication between such ports.

Analogously, the "white position" of the valve 51 refers to the valve position in which each of the shown three white-filled ring segments of the six-port valve serves as a fluid channel that provides fluid communication between the valve ports to which the concerning ring segment is connected. In the white position the three black-filled ring segments of the six-port valve do not provide such fluid communication between such ports.

Figure 7:
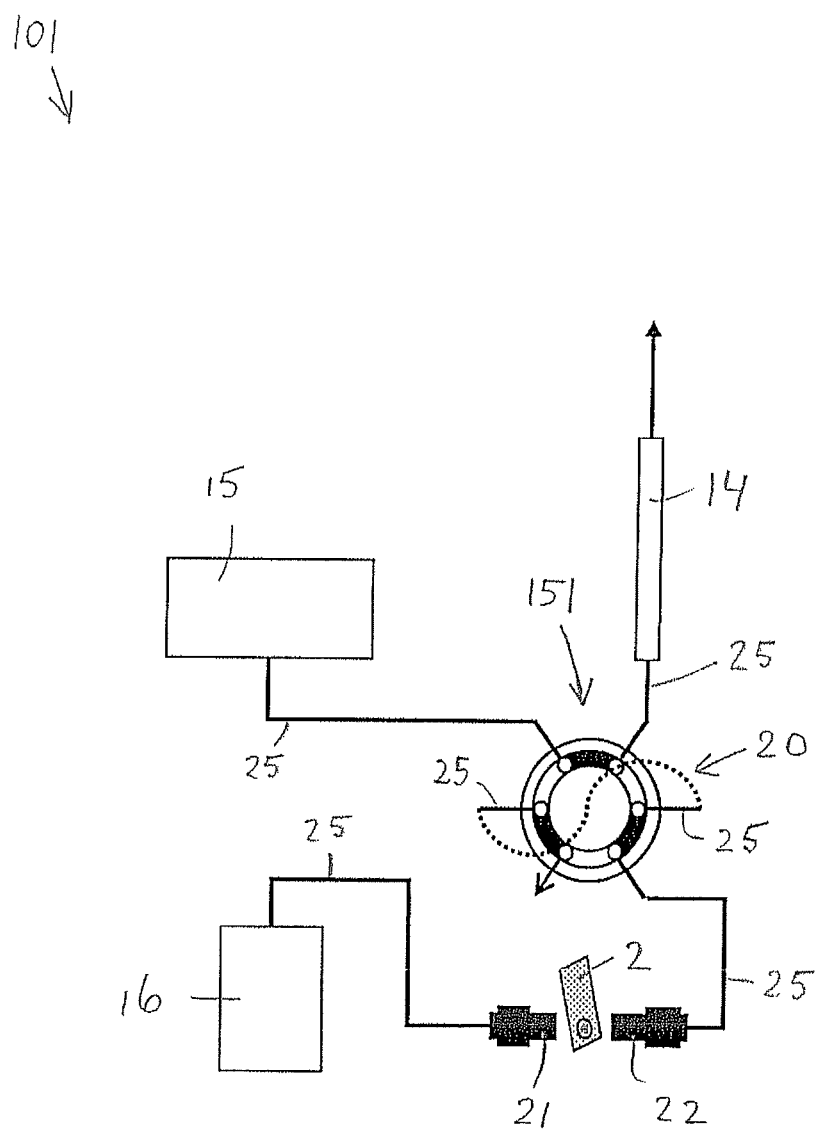
FIG. 7 shows an example of another embodiment of an apparatus for use in an example of another embodiment of a method according to the invention.
Figure 8:
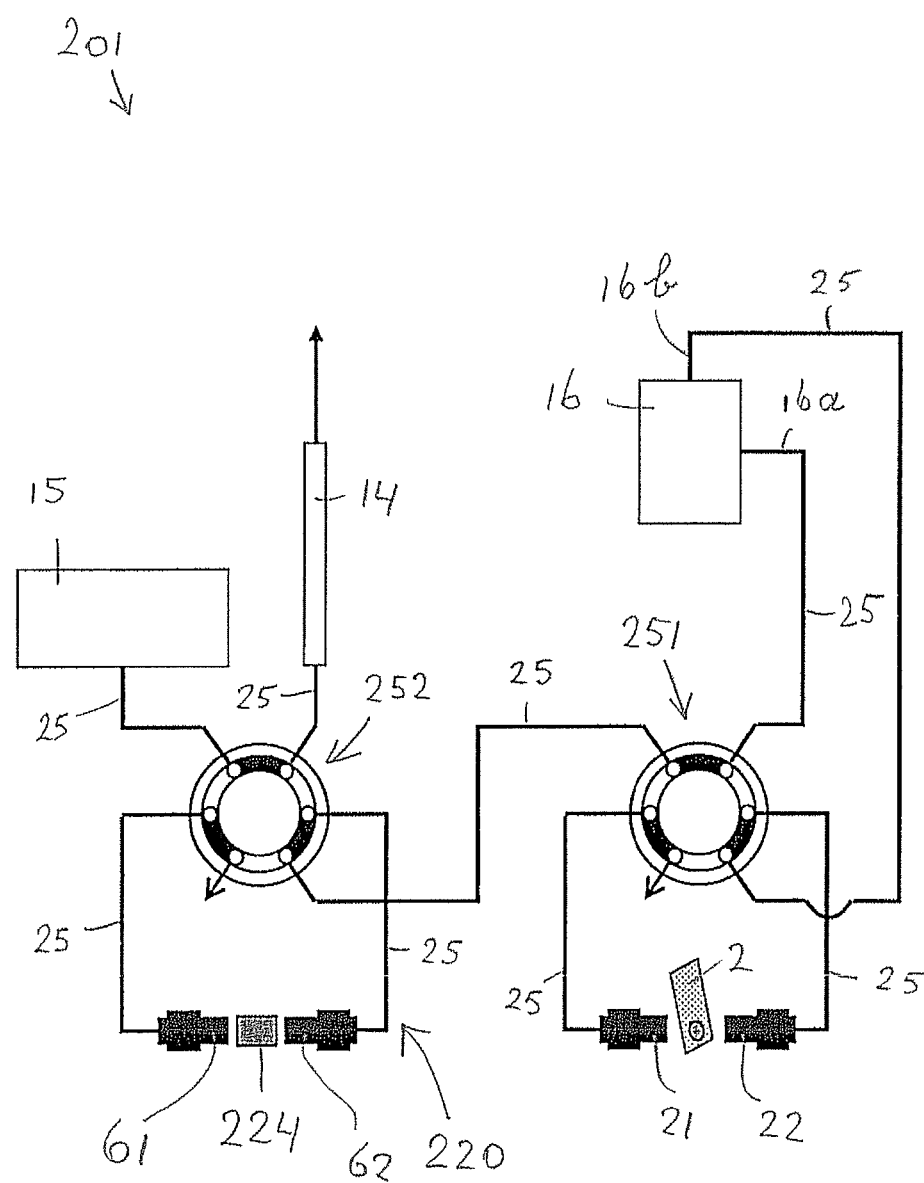
FIG. 8 shows an example of yet another embodiment of an apparatus for use in an example of yet another embodiment of a method according to the invention.

These terms "black position" and "white position" have been used with the same meanings for the similar six-port valves 151, 251 and 252 shown in FIGS. 7 and 8.

The apparatus 1 of FIG. 6 further comprises an automatic test sheet handling system 17 comprising at least one magazine 18 for storing a plurality of test sheets, such as the test sheet 2, and a pick and place mechanism 19. The pick and place mechanism 19 is arranged at least for: picking up test sheets from the at least one test sheet magazine 18, interposing such test sheet 2 inbetween the clamping heads 21, 22, precise positioning of such interposed test sheet 2 relative to the clamping heads 21, 22; moving such test sheet 2 away from the clamping heads 21, 22; and storing or discarding such test sheet 2.

It is remarked that, as mentioned above, embodiments are possible in which the test sheet in the clamped condition is sandwiched inbetween a first cover sheet and a second cover sheet. In such embodiments the automatic test sheet handling system 17 and/or the at least one magazine 18 and/or the pick and place mechanism 19 may additionally be arranged for handling and/or storing and/or pick and place such first and second cover sheets as well.

It is furthermore remarked that also each of the apparatus 101 and 201, shown in FIGS. 7 and 8, may comprise such an automatic test sheet handling system 17. For simplicity, such systems 17 have not been shown in FIGS. 7 and 8.

With the apparatus 1 of FIG. 6 it is possible to inject the desorbed and eluted blood sample together with a mobile phase into the column 14, wherein the sample elution fluid functions as said mobile phase and wherein the flushing of the desorption area 5 and said injecting into the column 14 are simultaneously driven by the action of the gradient pump 15. The following successive steps that may be carried out with the apparatus 1 are provided as an elucidating example.

(i) Initially, the valve 51 is in its "black position" (explained above).

(ii) Position a test sheet 2 inbetween the clamping heads 21, 22 and bring the clamping heads in clamping condition.

(iii) Switch valve 51 from its black position into its white position. Mobile phase delivered by the gradient pump 15 is now flowing via the clamping heads 21, 22 through the desorption area 5 of the sheet 2 towards the column 14.

(iv) After some time, the valve 51 is switched back into its black position. Mobile phase is now flowing directly from the gradient pump 15 towards the column 14 in order to analyse the blood sample by liquid chromatography.

(v) Wash the clamping heads 21, 22 by means of the dispenser 16 in order to remove possible remaining analyte and/or contaminants.

(vi) Move the clamping heads 21, 22 away from one another and remove the sheet 2 away from the interspace between the clamping heads.

Note that the successive steps (v) and (vi) can be performed in parallel with the liquid chromatography of step (iv).

Reference is now made to FIG. 7, which shows apparatus 101. Similar to the apparatus 1 of FIG. 6, the apparatus 101 of FIG. 7 comprises first and second clamping heads 21, 22, a compressive movement mechanism (not shown), a column 14, a gradient pump 15, a dispenser 16, a six-port valve 151, and a fluid conduit structure 25. Furthermore, the apparatus 101 comprises a sample loop 20 connected to the valve 151.

With the apparatus 101 of FIG. 7 it is possible to temporarily store at least the desorbed and eluted blood sample in the sample loop 20 and to inject at least part of the blood sample 3 stored in the sample loop 20, together with a mobile phase, into the column 14 for realizing said biomedical analysis, wherein said storing and said injecting is controlled by switching of the valve 151. The following successive steps that may be carried out with the apparatus 101 are provided as an elucidating example.

(i) Initially, the valve 151 is in its "black position" (explained above).

(ii) Position a test sheet 2 inbetween the clamping heads 21, 22 and bring the clamping heads in clamping condition.

(iii) Desorb and elute blood sample from the desorption area 5 of the clamped sheet 2 with a sample elution fluid delivered by the dispenser 16. The desorbed and eluted blood sample is now stored in the sample loop 20.

(iv-a) Switch valve 151 from its black position into its white position. Mobile phase is now flowing through the sample loop 20 towards the column 14 in order to analyse the blood sample, which was temporarily stored in the sample loop 20, by liquid chromatography.

(iv-b) In the meanwhile wash the clamping heads 21, 22 by means of the dispenser 16 in order to remove possible remaining analyte and/or contaminants.

(v) After some time, the valve 151 is switched back into its black position.

(vi) Move the clamping heads 21, 22 away from one another and remove the sheet 2 away from the interspace between the clamping heads.

Note that the liquid chromatography step (iv-a) can be performed in parallel with step (iv-b).

Reference is now made to FIG. 8, which shows apparatus 201. Similar to the apparatus 1 of FIG. 6, the apparatus 201 of FIG. 8 comprises first and second clamping heads 21, 22, a compressive movement mechanism (not shown), a column 14, a gradient pump 15, a dispenser 16, a six-port valve 251, and a fluid conduit structure 25. In the present embodiment the dispenser 16 has a first dispenser exit 16a and a second dispenser exit 16b. Furthermore, the apparatus 201 comprises a sample loop 220. The sample loop 220 is connected to the valve 251 and is furthermore integrated with an additional six-port valve 252 of the apparatus 201. In addition, the sample loop 220 comprises a disposable solid phase extraction cartridge 224 arranged between a corresponding clamping arrangement 61, 62 as known in the art.

With the apparatus 201 of FIG. 8 it is possible to remove undesired compounds of the blood sample prior to analysis. The following successive steps that may be carried out with the apparatus 201 are provided as an elucidating example.

(i) Initially, each of the valves 251 and 252 is in its "black position" (explained above).

(ii-a) Position a test sheet 2 inbetween the clamping heads 21, 22 and bring the clamping heads in clamping condition.

(ii-b) Place and clamp a solid phase extraction cartridge 224 between the clamping arrangement 61, 62.

(iii) Condition the cartridge 224 with fluids delivered by the dispenser 16 via its first dispenser exit 16a.

(iv) Switch valve 251 from its black position into its white position.

(v) Desorb and elute blood sample from the desorption area 5 of the clamped sheet 2, with a sample elution fluid delivered by the dispenser 16 via its first dispenser exit 16a, towards the cartridge 224.

(vi) Switch valve 251 from its white position into its black position.

(vii) Wash the cartridge 224 with a washing fluid delivered by the dispenser 16 via its first dispenser exit 16a, thus removing undesired compounds of the blood sample prior to analysis.

(viii) Switch the additional valve 252 from its black position into its white position. Under the action of the gradient pump 15, mobile phase is now flowing through the cartridge 224 towards the column 14 in order to analyse the blood sample by liquid chromatography.

(ix) In the meanwhile wash the clamping heads 21, 22 by means of the dispenser 16 via its second dispenser exit 16b in order to remove possible remaining analyte and/or contaminants, move the clamping heads 21, 22 away from one another and remove the sheet 2 away from the interspace between the clamping heads.

(x) After some time, switch the additional valve 252 from its white position into its black position.

Note that the successive steps (ii-b) and (iii) can be performed in parallel with step (ii-a).

In the foregoing specification, the invention has been described with reference to specific examples of embodiments of the invention. However, various modifications and changes may be made therein without departing from the broader scope of the invention as set forth in the appended claims.

It is for example possible to arrange the invention such that, instead of the shown circularly ring shaped imprinted sealing area, various other closed loop shapes are obtained, such as polygonal, oval, etcetera. Consequently, also various other shapes of the desorption area are possible.

Also, the dimensions, sizes and surface areas of the desorption area and the imprinted sealing area may vary.

Furthermore, it is possible to simultaneously create more than one imprinted sealing area and desorption area for a test sheet.

Also, the non-flat shape of the at least one of the first and the second outer surfaces may be realized in various other ways. For example, one of the first and the second outer surfaces could even be fully flat.

Furthermore, the opposing portions of the first and the second outer surfaces which through compression directly create the imprinted sealing area do not necessarily need to be flat. For example, these opposing portions may have mating undulations.

Also, a desorption area does not necessarily have to be in the center of a preprinted circular designation area on a test sheet. Off-center positions are also possible.

Furthermore it is possible to make arrangements for adding a low strength solvent (e.g. water) to the desorbed and eluted blood sample prior to its analysis. This allows the use of a sample elution fluid having high strength without compromising the analysis, such as (High Performance/High Pressure) liquid chromatography (HP)LC separation.

Also, arrangements may be made for using pre-heated sample elution fluid in order to enhance solubility of analytes without increasing the strength of the sample elution fluid. This helps to avoid disturbing the analysis, such as (HP)LC separation, with incompatible solvents.

Furthermore it is possible to pre-treat yet unused medical test sheets by creating one or more pre-imprinted sealing areas on them using clamping heads and a compressive movement mechanism. In that way, exactly known quantities of blood may be placed onto predefined desorption areas enclosed by pre-imprinted sealing areas, thus enabling accurate quantitative analyses.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word "comprising" does not exclude the presence of other features or steps than those listed in a claim. Furthermore, the words "a" and "an" shall not be construed as limited to "only one", but instead are used to mean "at least one", and do not exclude a plurality. The mere fact that certain measures are recited in mutually different claims does not indicate that a combination of these measures cannot be used to advantage.

What is claimed is:

1. An apparatus configured to desorb a blood sample from a medical test sheet having at least one dried blood spot thereon, for the purpose of biomedical analysis of the blood sample, the apparatus comprising:

a first clamping head with a first outer surface and a second clamping head with a second outer surface, the first and second outer surfaces facing towards one another; and a compressive movement mechanism configured to selectively move the first and the second clamping heads towards and away from one another, respectively, and configured to impart compressive forces to the first and the second clamping heads for clamping the test sheet inbetween the first and the second clamping heads when the test sheet, having first and second opposite faces, is interposed inbetween the first and second clamping heads such that the first face of the test sheet is facing towards the first outer surface, while the second face of the test sheet is facing towards the second outer surface;

an automatic test sheet handling system having at least one magazine configured to store a plurality of such test sheets, and a pick and place mechanism for at least: picking up test sheets from the at least one test sheet magazine, interposing such test sheet inbetween the clamping heads, precise positioning of such interposed test sheet relative to the clamping heads, moving such test sheet away from the clamping heads, and storing or discarding such test sheet, wherein:

at least one of the first and second outer surfaces has a non-flat shape configured such that the first and second clamping heads in clamped condition transmit the compressive forces to parts of the test sheet, in which the compressive forces are sufficient to create an imprinted sealing area of the test sheet, the imprinted sealing area having a closed loop shape surrounding a desorption area of the test sheet, the desorption area containing at least part of the at least one dried blood spot and the desorption area being contained in a space enveloped by the first and the second outer surfaces and sealed by the imprinted sealing area;

and the first clamping head includes a first fluid conduit extending therethrough and the second clamping head includes a second fluid conduit extending therethrough, each of the first and second fluid conduits ending in an enveloped space having the desorption area of the test sheet, the first clamping head and the second clamping head being configured to enable flushing of the desorption area of the clamped test sheet with a sample elution fluid such that the blood sample is desorbed and eluted from the desorption area via the first fluid conduit and the second fluid conduit.

2. The apparatus according to claim 1, wherein the compressive movement mechanism is configured to move the first and the second clamping heads towards one another such that in the clamped condition the shortest possible distance between the first and the second outer surfaces is less than 0.5 millimeter, preferably less than 0.2 millimeter, and more preferably less than 0.05 millimeter.

3. The apparatus according to claim 1, wherein the first outer surface and the second outer surface are substantially mirror images from one another.

4. The apparatus according to claim 1, wherein at least one of the first and the second outer surfaces has at least partly undergone an electrolytic polishing treatment.

5. The apparatus according to claim 1, wherein the non-flat shape of the at least one of the first and second outer surfaces is arranged such that the shortest possible distance, measured along the imprinted sealing area of the test sheet when travelling from portions of the test sheet interior of the closed loop to portions of the test sheet exterior of said closed loop, is at least 1.0 millimeter.

6. The apparatus according to claim 1, wherein transition portions of the at least one of the first and second outer surfaces are rounded off, in which the transition portions in the clamped condition are adjacent to and determine the transition between the imprinted sealing area and the desorption area of the test sheet.

7. The apparatus according to claim 1, further comprising:
analyzing means for realizing the biomedical analysis;
pumping means for realizing the flushing and injection of at least part of the desorbed and eluted blood sample together with a mobile phase into the analyzing means; and
a fluid conduit structure for realizing fluid communication at least between the pumping means, the first and second fluid conduits, and the analyzing means.

8. The apparatus according to claim 1, further comprising:
an analyzer configured to provide the biomedical analysis;
at least one pump configured to flush and inject at least part of the desorbed and eluted blood sample together with a mobile phase into the analyzer; and
a fluid conduit structure configured to enable fluid communication at least between the at least one pump, the first and second fluid conduits, and the analyzer.

* * * * *